United States Patent [19]

Neuenhofer et al.

[11] Patent Number: 5,834,206

[45] Date of Patent: *Nov. 10, 1998

[54] IMMUNOASSAYS FOR HAPTENS AND HAPTEN TRACER-ANTIBODY COMPLEX WHICH CAN BE USED THEREFOR, AND PROCESS FOR THE PREPARATION THEREOF

[75] Inventors: Stephan Neuenhofer; Reinhard Käsmarker, both of Marburg, Germany

[73] Assignee: Behring Diagnostics GmbH, Marburg, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 568,821

[22] Filed: Dec. 7, 1995

[30] Foreign Application Priority Data

Dec. 10, 1994 [DE] Germany ............... 44 44 002.2

[51] Int. Cl.$^6$ ................ G01N 33/53; G01N 33/48; A61K 38/00; C07K 16/00
[52] U.S. Cl. .................. 435/7.1; 530/807; 530/300; 530/387.1; 436/63; 436/543
[58] Field of Search ............... 435/7.1; 530/807; 530/300, 387.1; 436/63, 543

[56] References Cited

U.S. PATENT DOCUMENTS

| 4,645,646 | 2/1987 | Gadow et al. | 422/61 |
| 4,657,873 | 4/1987 | Gadow et al. | 436/532 |
| 5,302,533 | 4/1994 | Kricka | 436/537 |

FOREIGN PATENT DOCUMENTS

| 0 073 593 | 3/1983 | European Pat. Off. . |
| 0 135 071 B1 | 3/1985 | European Pat. Off. . |
| 0 442 372 B1 | 8/1991 | European Pat. Off. . |
| A-442372 | 8/1991 | European Pat. Off. . |
| 0 487 301 | 5/1992 | European Pat. Off. . |
| WO 93/20074 | 10/1993 | WIPO . |

OTHER PUBLICATIONS

Nargessi et al., "Use of Antibodies Against the Label in Non–separation Non–isotopic Immunoassay: 'Indirect Quenching' Fluoroimmunoassay of Proteins," *Chemical Abstracts*, Abstract No. 71265, vol. 91, (Aug. 27, 1979).

Ishidawa et al, "Novel and sensitive noncompetitive (two–site) immunoassay for haptens with emphasis on peptides" Clin. Biochem., vol. 23, pp. 445–453, Oct. 1990.

*Primary Examiner*—Sheela Huff
*Assistant Examiner*—Yvonne Eyler
*Attorney, Agent, or Firm*—Finnegan, Henderson, Farabow, Garrett & Dunner, L.L.P.

[57] ABSTRACT

There are disclosed hapten tracer complexes which, on the one hand, contain a hapten which is linked to an indicator component and, on the other hand, an antibody which can bind specifically to the indicator component. These hapten tracer complexes can be employed advantageously in immunoassays.

16 Claims, 9 Drawing Sheets

Fig.3  Luminescence immunoassay for the determination of FT3 (Example 1: IgG, c.t.)

Fig. 4 Luminescence immunoassay for the determination of FT3 (Example 2: IgG, magnetic particles)

Fig. 6 Luminescence immunoassay for the determination of FT3 (Example 3: Fab, c.t.)

Fig. 7  Luminescence immunoassay for the determination of FT3 (Example 4: Fab, magnetic particles)

Fig. 8a  Signal stability of the free and of the complexed T3 hapten tracer

Fig. 8b  Signal stability of the free T3 hapten tracer

IMMUNOASSAYS FOR HAPTENS AND HAPTEN TRACER-ANTIBODY COMPLEX WHICH CAN BE USED THEREFOR, AND PROCESS FOR THE PREPARATION THEREOF

The present invention relates to the area of immunoassays. It is frequently desirable to detect whether a certain antigen, i.e. a compound which can cause an immunological reaction, is present in a sample or not. The detection of the antigen is often performed by means of so-called immunoassays, the antigen or the hapten being detected with the aid of immunological methods. The present invention in particular relates to immunoassays in which so-called hapten tracer complexes are employed. In the hapten tracers, the immunologically relevant hapten is linked to an indicator component.

Chemiluminescently labeled hapten conjugates are known from the prior art. EP 0 135 071 describes chemiluminescently labeled hapten conjugates which between the group capable of chemiluminescence and the hapten have a linking group, which is also called a "spacer". The connection group is a chain-like polymer having recurring functional groups such as peptides, glycoproteins, glycolipids or carbohydrates.

EP 0 442 372 describes labeled haptens in which an indicator component designated as a label is linked to the hapten via a polyethylene glycol and a protein or oligo- or polypeptide. The indicator component is a group which can be quantified by chemical or physical methods.

It was found that the haptens linked to an indicator component in practice have certain disadvantages. Thus, as a rule, these hapten conjugates are not stable on storage, in particular if aqueous solutions are concerned, and storage in the deep-frozen state is not carried out, as there is the risk of hydrolysis. It was furthermore found that hapten conjugates of this type frequently yield nonreproducible results on account of nonspecific binding. In some cases the nonspecific binding of hapten tracers to vessel walls can indeed be reduced by appropriate additives, for example proteins, but these additives not uncommonly adversely affect the quality of the test.

In practical use, further problems can also result in that the user of the test solutions pools several tracer solutions for a larger batch. Owing to the use of a further vessel, uncontrolled adsorption phenomena then again occur, whose extent can depend on the type (glass, polyethylene, polystyrene etc.) and size of the vessel used and on the temperature. As a result, the suitability of the hapten tracer in the test assay can no longer be guaranteed.

The present invention therefore relates to hapten tracer complexes which on the one hand contain a hapten which is linked directly or via a spacer group to an indicator component and on the other hand contain an antibody which can bind specifically to the indicator component.

An indicator component is a signal-transmitting component which can also be designated as a label or marker.

The hapten tracer complexes according to the invention consist on the one hand of a hapten which is linked directly or via a spacer group to an indicator component. Hapten is a description for an antigen which, on account of its size, as a rule can only induce the formation of antibodies after coupling to a carrier. The indicator component is a group which is detectable or quantifiable by chemical or physical methods. Hapten and indicator component can either be bonded directly via a chemical bond; or a spacer group, also called a spacer, can be located between the two components. Customarily, spacer groups used are linear structures, for example polyethylene glycol. However, it is perfectly possible to use other chain-like polymers having recurring functional groups, such as peptides, glycoproteins, glycolipids or carbohydrates, as spacer groups. Typical examples of spacer groups of this type are polysaccharides such as dextrans, pectins, lectins, peptides such as polylysine, proteins such as serum albumin or globulins, or glycoproteins such as transferrin.

The hapten tracer complexes according to the invention furthermore contain an antibody which can bind specifically to the indicator component. Antibodies of this type, which are specific for the indicator component, are obtained by immunological methods known per se. Polyclonal antibodies which are directed against the indicator component are obtained by immunizing laboratory animals, for example rabbits, with the indicator component (preferably a label-protein conjugate). Alternatively to this, monoclonal antibodies which are specifically directed against the indicator component can be prepared by the known process of Köhler and Milstein.

The hapten tracer complexes according to the invention can basically be used in all appropriate immunoassays, advantageously in heterogeneous immunoassays. In these tests, an antibody which is specific for the antigen or hapten to be detected is coupled to a solid phase either via a covalent bond or by adsorption. This antibody, which is specific for the hapten, is preferably obtained by covalently coupling this hapten to a polymer, for example to serum albumin, and immunizing the animal selected for antibody production with it. It has been shown that antibodies of this type are highly specific both for the pure hapten and for the hapten linked to an indicator component. Suitable haptens are all organic substances of analytical interest which can cause an immunological reaction in a host animal when they are injected in the form of an immunogenic conjugate of the hapten and a carrier molecule for immunization.

As a rule, the antibody specific for the hapten is bonded to a solid carrier. Examples of carriers of this type are polystyrene tubes or beads to which the antibody is attached by adsorption, or plastic surfaces pretreated with lysine-containing polypeptides to which the antibody is covalently bonded via bifunctional reagents or magnetic latex particles functionalized with $NH_2$ groups or COOH groups, to which the antibody is bonded, for example, with the aid of carbodiimides.

In a preferred embodiment of the present invention, the indicator component is a group capable of chemiluminescence, this group being particularly preferably selected from the group comprising acridinium acylsulfonamide, acridinium ester, luminol, isoluminol, dioxetane, oxalic acid ester or oxalamide or a derivative of one of these compounds.

Chemiluminescence is understood as meaning the emission of light in a chemical reaction. In the context of the present invention, those compounds are therefore bonded to the hapten which are capable of chemiluminescent reactions. These can be an acridinium ester, acridinium acylsulfonamide, luminol or its derivatives, an isoluminol or its derivatives, a dioxetane, a luciferin, an oxalic acid ester or an oxalamide.

In another preferred embodiment, the indicator component is a group capable of fluorescence. In this case, the indicator component used is a fluorescent dye. An example of a fluorescent dye of this type is fluorescein isothiocyanate.

In another preferred embodiment, the indicator component is a group capable of bioluminescence. Bioluminescence is a form of luminescence which occurs in lower organisms such as bacteria, fungi, coelenterates, worms, crustaceans etc. In bioluminescence, luciferin is generally converted enzymatically by luciferases in the presence of oxygen with ATP consumption into activated oxyluciferin, which forms oxyluciferin with emission of light (visible blue light).

In another embodiment of the present invention, the indicator component can be a group which is capable of electroluminescence. Electroluminescence is produced by electric field strengths.

In a further embodiment of the present invention, the indicator component is capable of phosphorescence. In phosphorescence, electronically excited inorganic or organic compounds emit the absorbed energy again in the form of radiation of usually longer wavelength at the earliest $10^{-3}$ seconds after excitation.

In the context of the present invention, the antibodies directed against the indicator component can be monoclonal antibodies, polyclonal antibodies, antibody fragments, chemically modified antibodies or chemically modified antibody fragments.

The hapten tracer complexes according to the invention can be prepared in a simple manner. Preferably, the hapten tracer-antibody complexes according to the invention are prepared by bringing together the antibody directed against the indicator component and the labeled hapten derivative in aqueous solution. The aqueous reaction solution can optionally contain organic solvents for improving the solubility of the hapten tracer in concentrations of greater than 0 to approximately 50%. Acetonitrile, dimethylformamide or dimethyl sulfoxide are preferably employed here.

The present invention also relates to test kits which are suitable for carrying out immunoassays for the detection of an antigen or hapten. It is essential that at least one hapten tracer-antibody complex according to the invention is employed in this case.

Test kits in the sense of the present invention are understood as meaning those entities which are necessary for carrying out an immunoassay. As a rule, the test kits comprise an article which has a solid phase, such as microtiter plates, polystyrene tubes or the like, at least one antibody which is directed against the hapten and at least one hapten tracer-antibody complex according to the invention.

In a preferred embodiment, the test kits according to the invention furthermore comprise those components which are necessary for carrying out a luminescence immunoassay.

In a particularly preferred embodiment, the test kits according to the invention also comprise magnetizable particles. As a rule, immunoassays of this type are carried out in test-tubes. In this case, the antibody directed against the hapten is bonded to particles which can be attracted by a magnet. Preferably, these are magnetizable latex beads which can contain magnetite particles which are coated by polystyrene, the diameter of the latex bead being up to 5 $\mu$m, preferably, 0.5 to 2 $\mu$m. These antibody magnetic particles are brought into contact with the fluid to be investigated and can be conveniently precipitated with the aid of a magnet after reaction.

As a rule, the immunoassays according to the invention are competitive heterogeneous immunoassays. In this case, the antibody directed against the hapten is coupled to a solid phase which is brought into contact with the sample to be investigated. A defined amount of a hapten which is linked to an indicator component is additionally added to the sample. If no hapten is present in the sample to be investigated, all antibodies can react with hapten which contains an indicator component; the maximum signal will therefore occur in the sample to be investigated in the absence of the analyte.

If the sample contains a higher concentration of hapten, the hapten present in the sample competes with the hapten which is linked to the indicator component. The more free hapten in the sample, the less hapten which is bonded to an indicator component can bind to the solid phase and therefore the weaker the signal. The actual concentration of hapten in the sample to be investigated can be determined by means of appropriate calibration curves.

The hapten tracer-antibody complexes according to the invention are therefore suitable for use in an immunoassay for the detection of an antigen or hapten, as a rule this being a competitive immunoassay. In the immunoassays, the luminescence can be measured by methods known per se as a function of the respective indicator components. In the case of the acridinium acylsulfonamide preferably used, the measurement of the luminescence can be carried out, for example, by bringing the appropriate solid phase into contact with an alkaline hydrogen peroxide solution or with an acidic hydrogen peroxide solution with an immediately following pH increase. The photoreaction occurring here can be measured in known apparatuses, for example the BERILUX® analyzer. It has been shown that the handling, sensitivity and precision of luminescence immunoassays of this type for haptens is completely comparable with that of corresponding radio-immunoassays, it being possible in the luminescence immunoassays according to the invention to avoid the use of radioactive components. Moreover, the luminescence immunoassays according to the invention are suitable for automation and can also be used, in fully automatic systems.

The hapten tracer-antibody complexes according to the invention have a number of advantages when used in immunoassays. First, the hapten tracer-antibody complexes are simple to prepare. The haptens linked to the indicator component are brought together with the antibody in aqueous solution. A specific reaction takes place here between the indicator component and the binding region of the antibody. If monoclonal antibodies are used against the indicator component, the possibility also results of affecting the signal via the choice of the antibody.

The hapten tracer-antibody complexes according to the invention have a defined incorporation rate. In the case of an IgG antibody, two molecules of hapten-indicator component can be bound per molecule of anti-indicator component antibody. In the case of a Fab fragment, the incorporation rate is reduced to one molecule of hapten-indicator component per molecule of anti-indicator component antibody fragment. By the use of a submolar amount of hapten-indicator component, however, the incorporation rate can also be reduced controllably.

Owing to the presence of the antibody directed against the indicator component, the hydrophilicity of the complex is increased. The hydrophobic properties of the hapten tracer-antibody complex are distinctly lower than those of the free hapten tracer on account of the high protein content and usually additionally owing to the direct binding of the indicator part, which, as a rule, is hydrophobic, to the specific binding region of the anti-indicator component antibody. This has a positive effect on the water solubility of the tracer and leads to a lesser extent to nonspecific binding. An increased measuring accuracy can thus be achieved as a result of the complex according to the invention.

A further advantage of the complex according to the invention is that an increased stability of the complex can be achieved. Even in the case of hapten tracers whose indicator component is sensitive to hydrolysis, a more or less pronounced decrease in the signal activity is seen on relatively long storage in aqueous solution. As a rule, the binding of the indicator component to the specific binding region of the anti-indicator component antibody is linked to a significant protection against hydrolysis.

The incorporation, which is simple to carry out, of two indicator components per antibody molecule or of one indicator component per Fab fragment leads to hapten tracer-antibody complexes which have a signal activity.

The present invention is illustrated by the following examples.

EXAMPLE 1

(IgG; coated tubes)
A) Preparation of a T3 (=triiodothyronine) hasten tracer

Figure 1A:
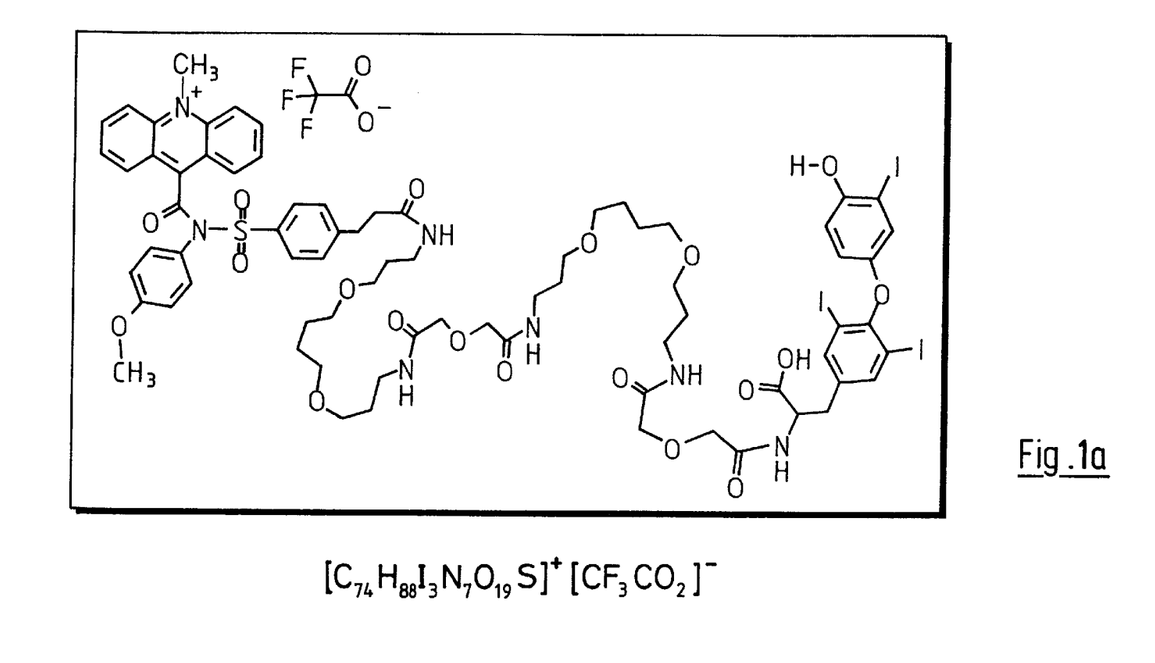
FIG. 1a shows the structural formula of an acridinium acylsulfonamide-labeled triiodothyronine.

The structural formula of the acridinium acylsulfonamide-labeled triiodothyronine prepared is shown in FIG. 1a.

Figure 1B:
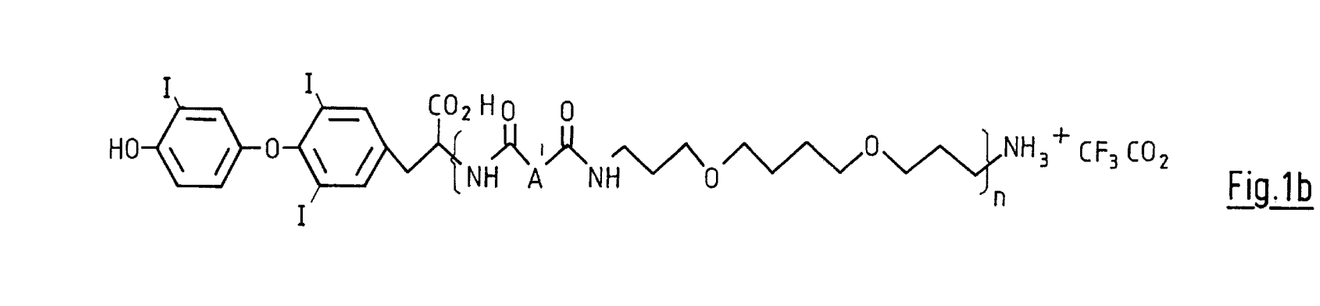
FIG. 1b shows the structural formula of a T3 derivative.

220 mg (0.162 mmol) of T3 derivative which is shown in FIG. 1b, in which A' has the meaning —$CH_2$—O—$CH_2$— and n has the value 2 (also described in EP 0 442 372), are initially introduced into 3 ml of dry N,N-dimethylformamide (DMF), a solution of 124 mg (0.162 mol) of BERILUX® label (containing an N-hydroxysuccinimidyl reactive group) in 2 ml of DMF is added and the mixture is stirred for 48 h at room temperature. The solvent is distilled off in an oil pump vacuum. The residue is purified by preparative medium-pressure chromatography (Büchi system) on a reversed phase column [stationary phase: LichroPrep C-18 (Merck); mobile phase: methanol/water=70:30+0.1 % by volume of trifluoroacetic acid]. 167 mg (52%) of yellow-orange powder are isolated. $[C_{74}H_{89}I_3N_7O_{19}S]^+(1792)[CF_3CO_2]^-(113)$; MS: (FAB) 1792 ($M^+$).

B) Preparation of the T3 hasten tracer-antibody complex
a) Anti-indicator component antibody Monoclonal mouse antibody (BW 90-9/016, Behringwerke AG, Marburg), directed against the BERILUX® label, dissolved in 0.5M sodium acetate, 0.5M NaCl, 50 mM tris HCl, pH 7.0, 0.01 % sodium azide. The concentration of the antibody was 11.5 mg/ml.

b) Preparation and purification

Figure 2:
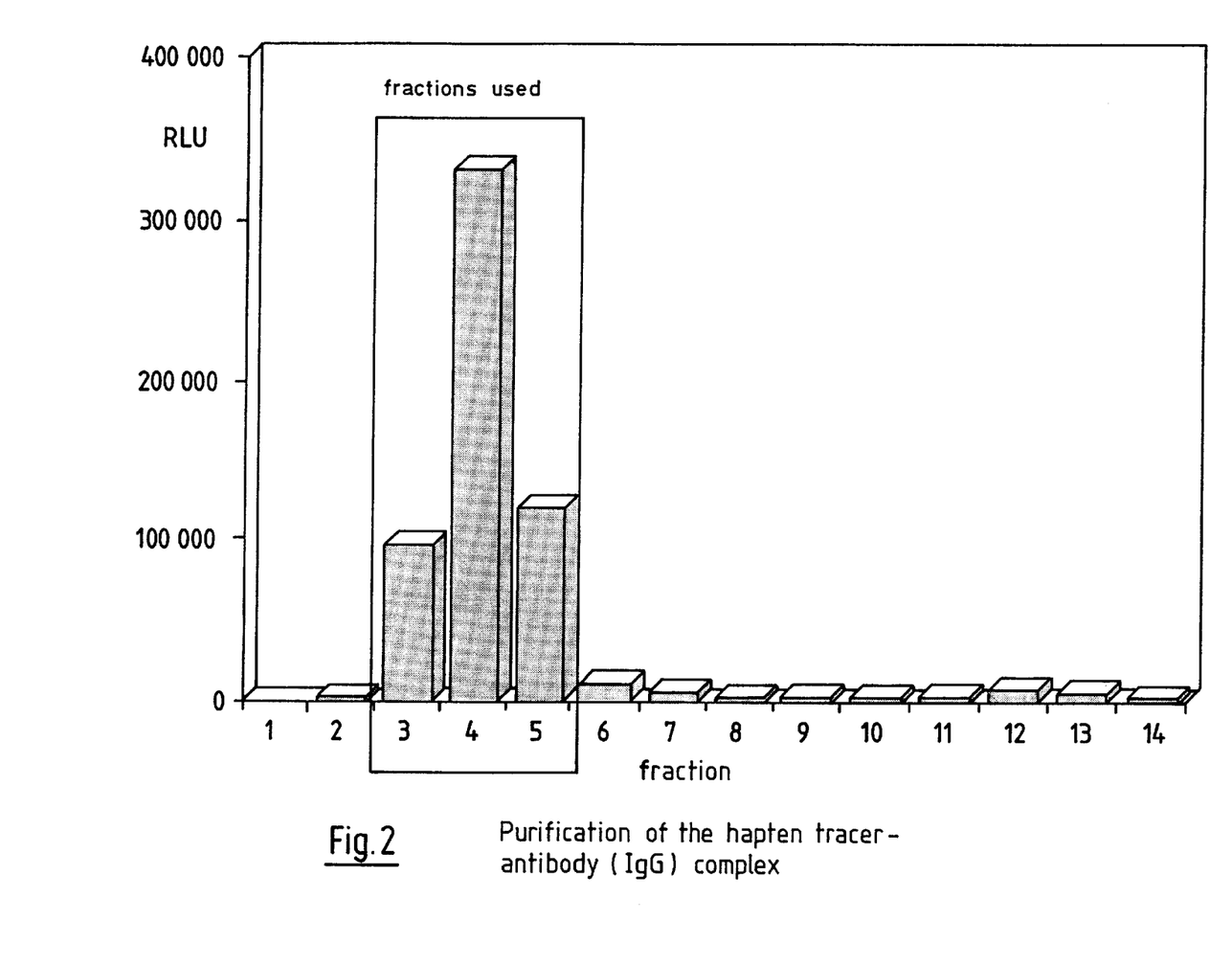
FIG. 2 shows purification of the hapten tracer-antibody (IgG) complex.

600 µl of incubation buffer (10 mM phosphate, 8 g of NaCl/l, 0.2 g of KCl/l, pH 7.3), 8.7 µl of anti-label antibody solution (see a), 60 µl of acetonitrile and 2.5 µl of T3 hapten tracer (A) (1 mg/ml of acetonitrile) are mixed and incubated for 15 minutes at RT. Purification is carried out by gel chromatography (PD-10 Sephadex G-25M; code no. 17-0851-01, bed volume 9 ml, fraction size 0.5 ml). The elution profile is shown in FIG. 2.

C) Use of the T3 hasten tracer-antibody complex in a luminescence immunoassay for the determination of FT3 (free content of triiodothyronine)
a) Solid phase The solid phase used was the coated tubes of the BERILUX® FT3 kit.

b) Tracer

The tracer described under B) was stored in a concentration of 150 ng/ml of BERILUX® FT3 tracer buffer.

c) FT3 standards

The FT3 standards were employed at a concentration in the range 0 to 50 pg/ml of serum matrix.

d) Assay procedure

Figure 3:
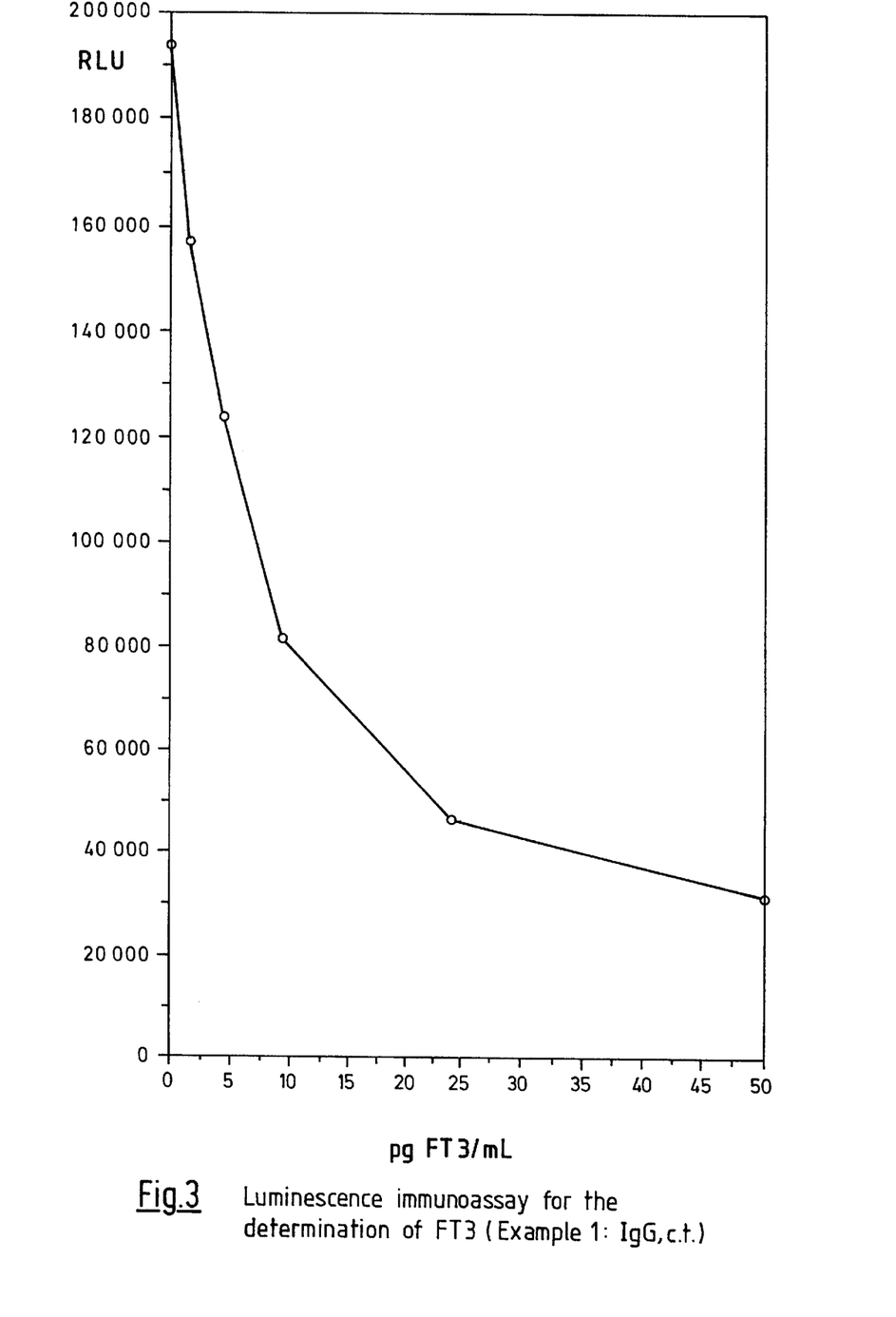
FIG. 3 shows a luminescence immunoassay for the determination of FT3.

100 µl of sample and 200 µl of BERILUX® FT3 incubation buffer were pipetted into BERILUX® FT3 coated tubes. The tubes were shaken (300 rpm) for 30 minutes at RT (room temperature). After washing twice with 0.5 ml of PBS buffer each time, 200 µl of tracer were pipetted in and the mixture was shaken for a further 5 minutes at RT. After washing three times with 0.5 ml of PBS buffer each time, the tubes were measured in the BERILUX® analyzer. The results are shown in FIG. 3 (RLU is "Relative Light Units").

EXAMPLE 2

(IgG; magnetic particles)
A) and B)
As in Example 1.
C) Use of the T3 hasten tracer-antibody complex in a luminescence immunoassay for the determination of FT3
a) Solid phase Magnetic particles from Rhone-Poulenc (Item No. EM1-100/20) were coated with a monoclonal anti-T3 antibody (BERILUX® FT3 antibody) by the carbodiimide method [G. Wendlberger, P. Steizel, Synthesis of peptides, part II (Methods of Org. Chem.) Houben-Weyl, 4th ed. 1952, Vol. XV/2, 1974]. The coating concentration was 0.25 mg of antibody per ml of 10% strength magnetic particle suspension. The ready-to-use suspension had a magnetic particle concentration of 2.5 mg per ml of storage buffer (10.36 g of CHES, 0.5 g of sodium azide, 1 g of bovine IgG per liter, pH 8.0).

b) and c) Tracer and FT3 standards
As in Example 1.
d) Assay procedure

Figure 4:
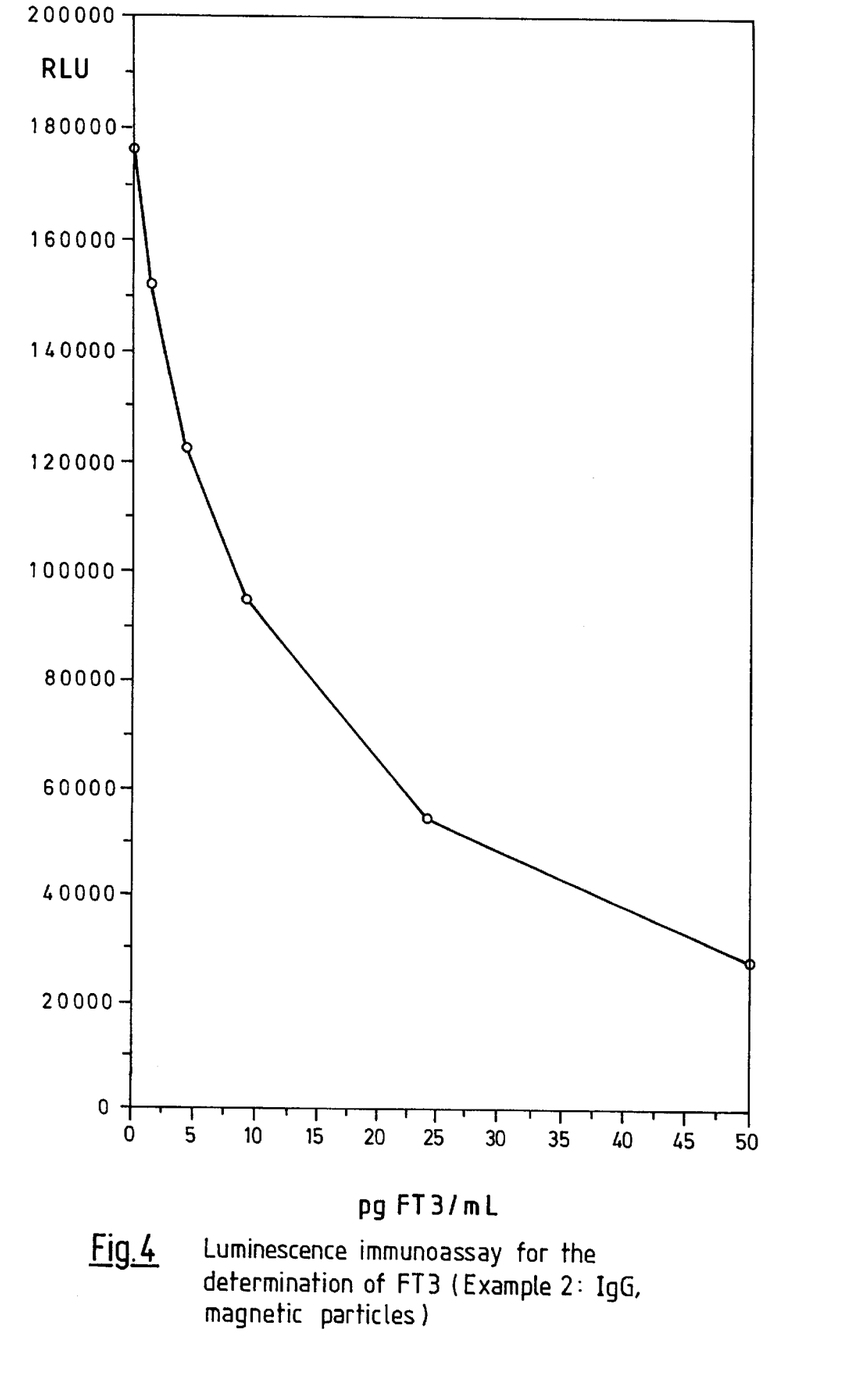
FIG. 4 shows a luminescence immunoassay for the determination of FT3.

20 µl of coated magnetic particles (a), 100 µl of sample and 200 µl of BERILUX® FT3 incubation buffer were incubated in a polystyrene tube for 30 minutes at 37° C. After washing the solid phase twice with 0.5 ml of PBS buffer each time, 200 µl of tracer were added and the mixture was incubated for 5 minutes at RT. After washing three times with 0.5 ml of PBS buffer each time, the tube was measured in the BERILUX® analyzer. The results are shown in FIG. 4.

EXAMPLE 3

(Fab; coated tubes)
A) Preparation of the T3 hasten tracer
As in Example 1.
B) Preparation of the complex of T3 hasten tracer and antibody Fab fragment
a) Anti-indicator component antibody (Fab fragment)

Fab fragment obtained by papain cleavage of the monoclonal mouse antibody (BW 90-9/016, Behringwerke AG, Marburg), directed against the BERILUX® label, is dissolved in 0.5M sodium acetate, 0.5M NaCl, 50 mM tris HCl, pH 7.0, and 0.01 % sodium azide. The concentration of the Fab fragment was 1 mg/ml.

b) Preparation and purification

Figure 5:
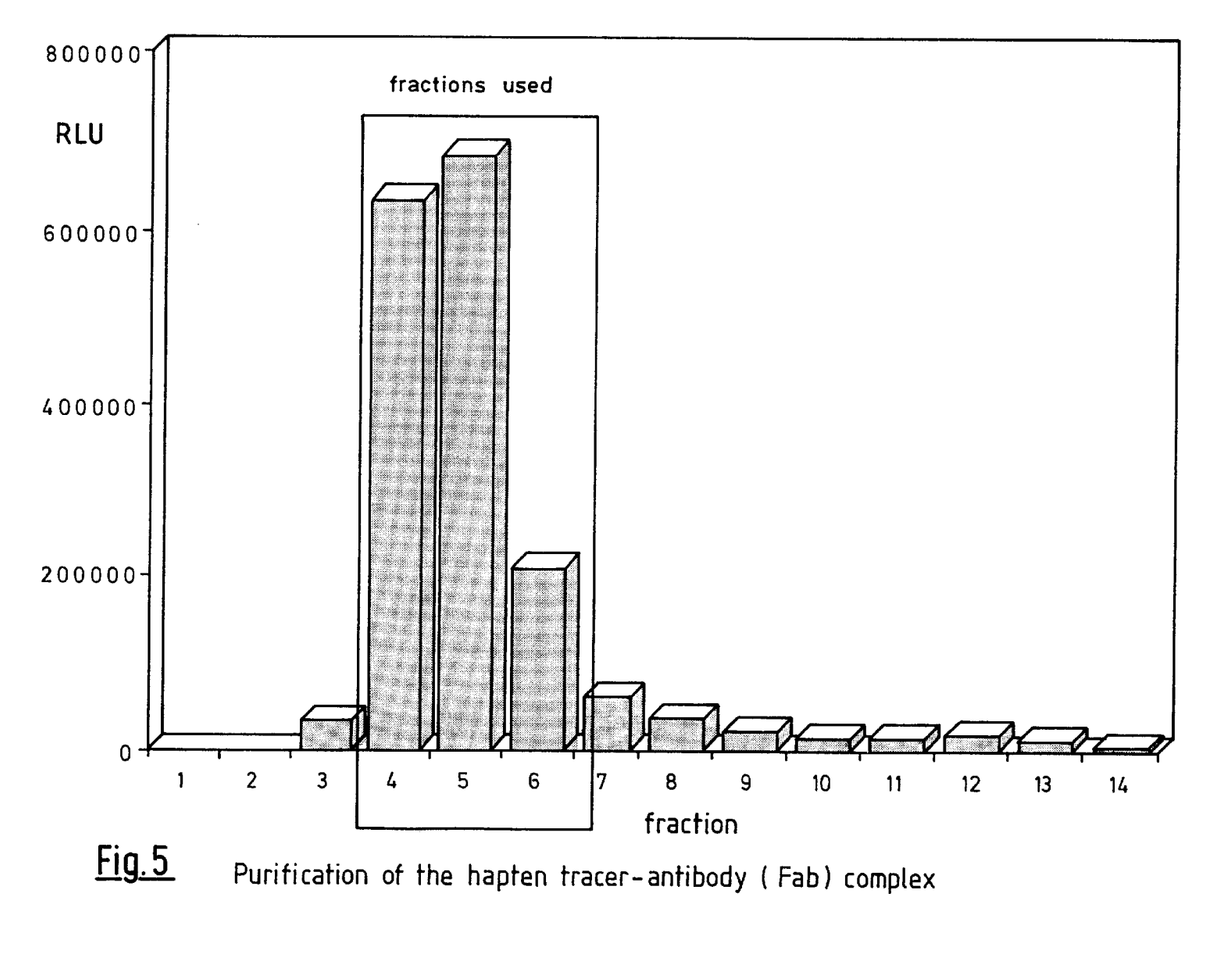
FIG. 5 shows purification of the hapten tracer-antibody (Fab) complex.

500 µl of incubation buffer (10 mM phosphate, 8 g of NaCl/l, 0.2 g of KCl/l, pH 7.3), 100 µl of anti-label antibody (Fab) solution (see a), 60 µl of acetonitrile and 7.6 µl of T3 hapten tracer (A) (1 mg/ml of acetonitrile) are mixed and incubated for 15 minutes at RT. Purification was carried out by gel chromatography (PD-10 Sephadex G-25M; code no. 17-0851-01, bed volume 9 ml, fraction size 0.5 ml). The elution profile is shown in FIG. 5.

C) Use of the T3 hasten tracer antibody-Fab fragment complex in a luminescence immunoassay for the determination of FT3 a)–d) Solid phase, tracer, FT3 standards and assay procedure

Figure 6:
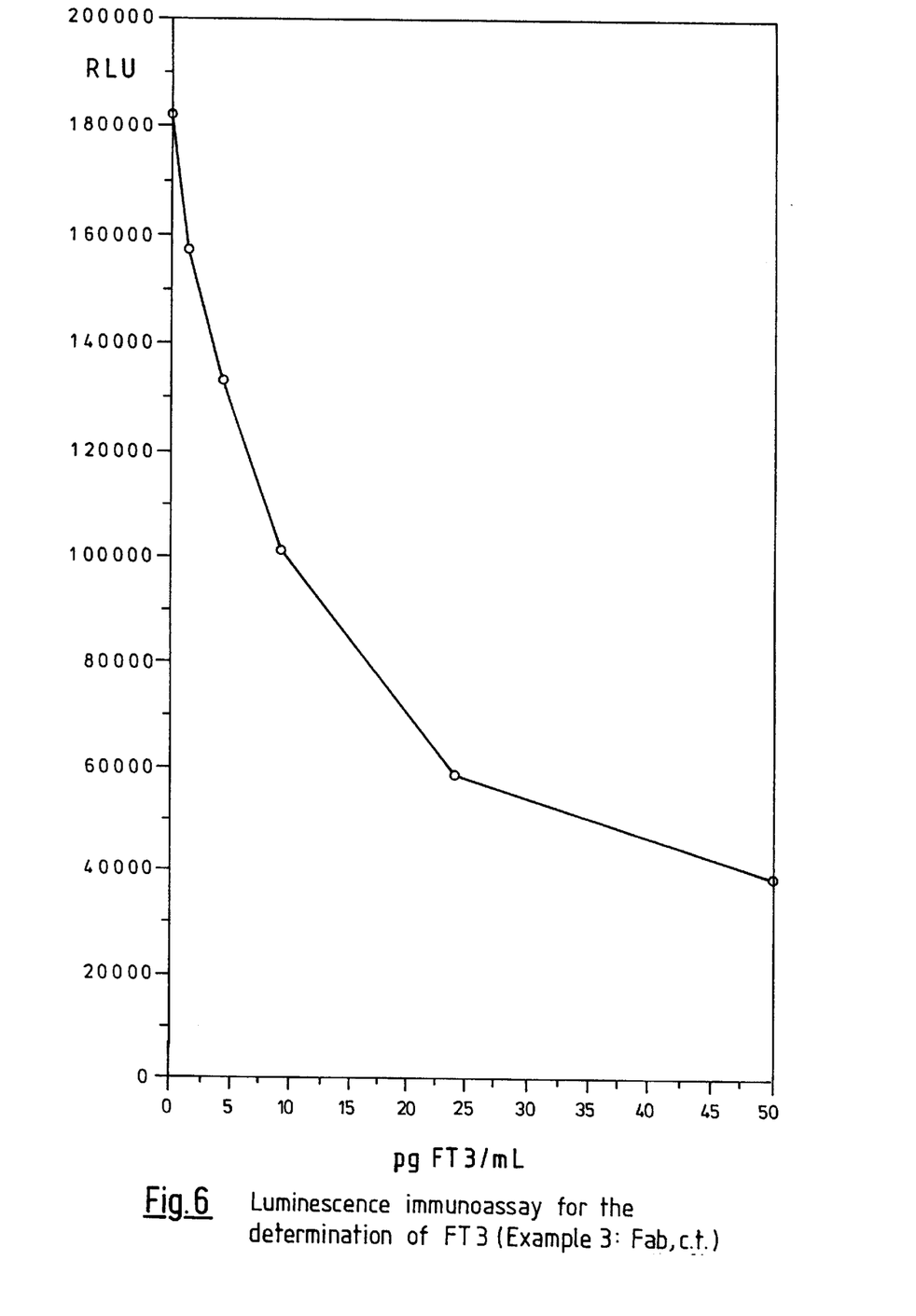
FIG. 6 shows a luminescence immunoassay for the determination of FT3.

As in Example 1, but using a tracer concentration of 50 ng/ml. The standard curve is shown in FIG. 6.

EXAMPLE 4

(Fab; magnetic particles)

A) and B)

As in Example 3.

C) Use of the T3 hasten tracer antibody-FAB fragment complex in a luminescence immunoassay for the determination of FT3 a)–d) Solid phase, tracer, FT3 standards and assay procedure

As in Example 2.

Figure 7:
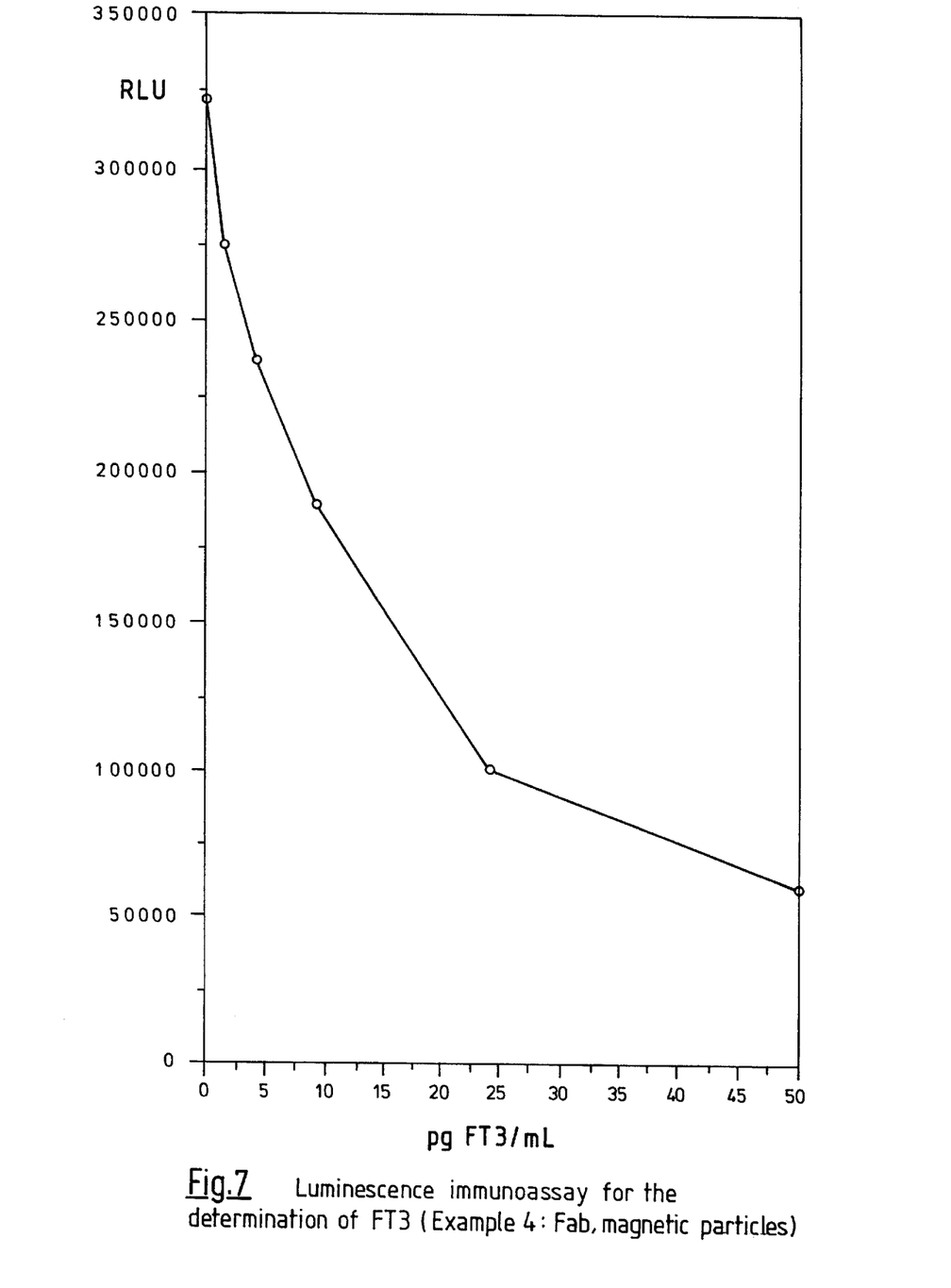
FIG. 7 shows a luminescence immunoassay for the determination of FT3.

The standard curve is shown in FIG. 7.

EXAMPLE 5

(Signal stability of the free hapten tracer)

In order to indicate the instability of a hapten tracer solution (solution which contains the free hapten tracer, i.e. not complexed by the anti-label antibody), 0.3 mg of T3 hapten tracer, as shown in FIG. 1a, were dissolved in 0.3 ml of acetonitrile to give a clear solution (1 mg/ml). This solution was diluted with tracer buffer (100 mM phosphate buffer, pH 6.3 containing 8.8 g of NaCl/l, 1 g of Mergal K9N/l, 2 g of bovine IgG/l) to a concentration of 10 ng of T3 hapten tracer per ml (=stock solution).

Figure 8A:
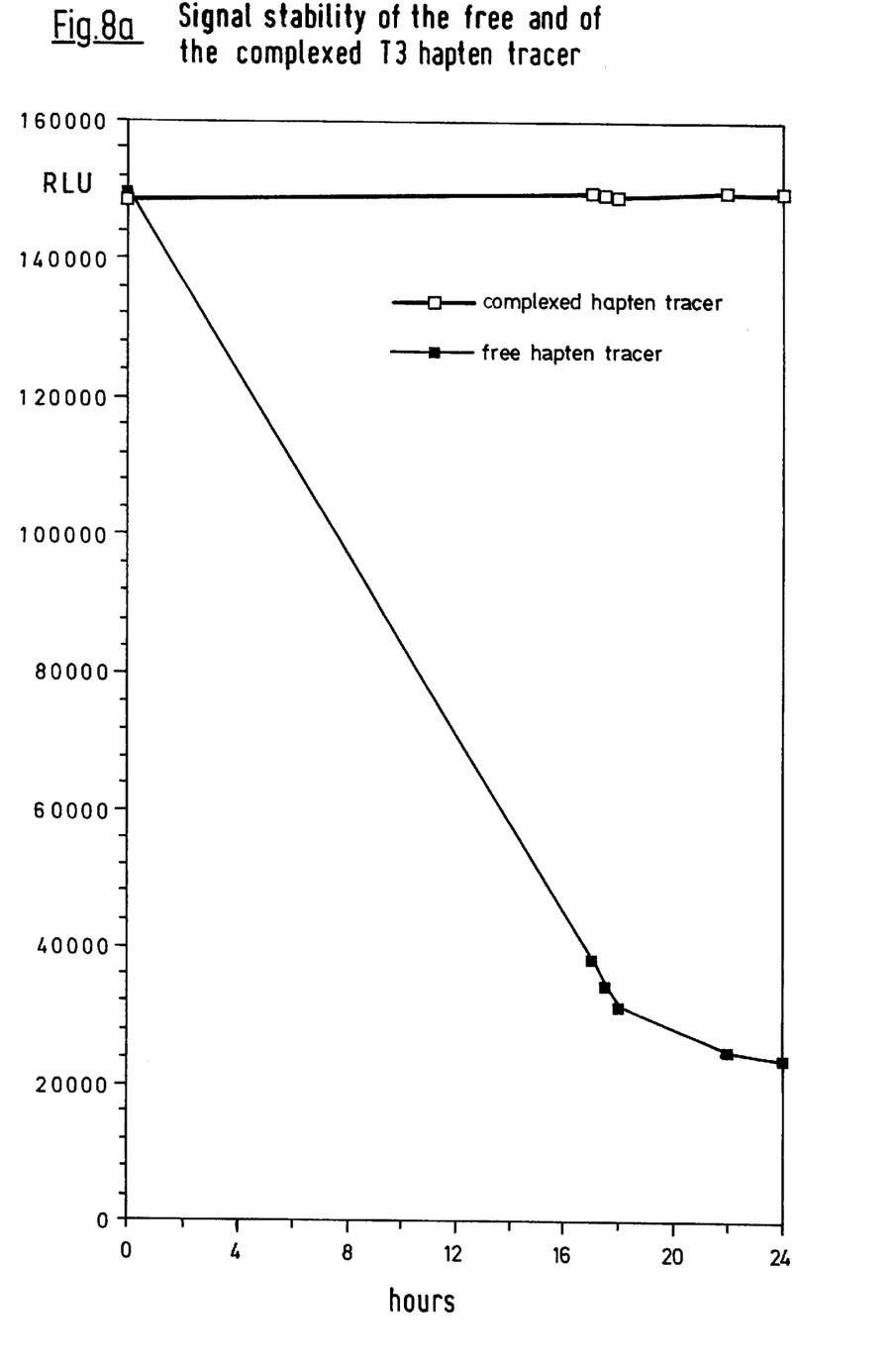
FIG. 8a shows signal stability of the free and of the complexed T3 hapten tracer.

After various times, samples were taken from this stock solution and measured in a luminometer. FIG. 8a shows clearly that despite the presence of protective protein in the form of immunoglobulin the signal activity decreased rapidly from sample to sample. The signal of the complexed hapten tracer, on the other hand, remains constant.

Figure 8B:
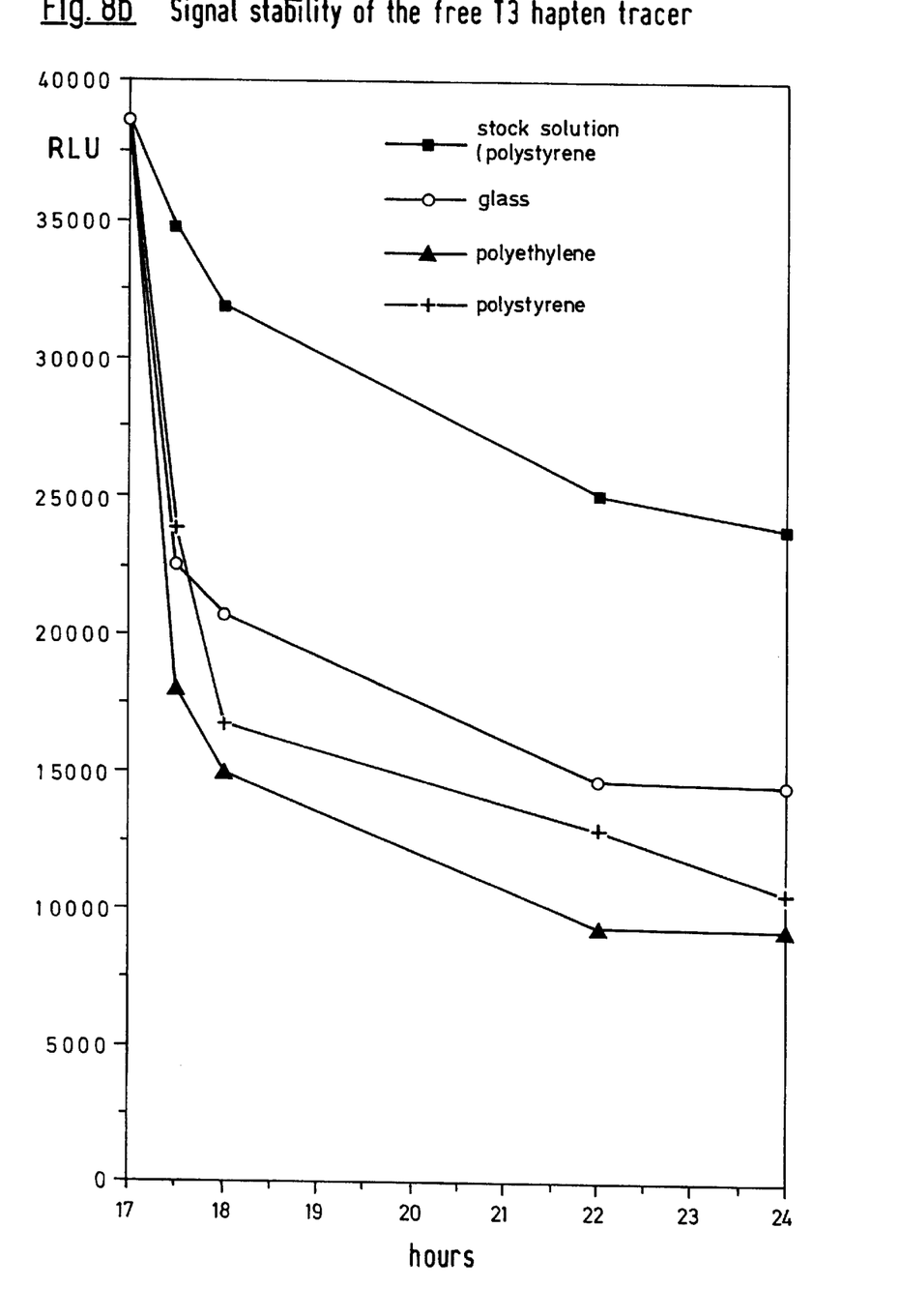
FIG. 8b shows signal stability of the free T3 hapten tracer.

After 17 hours, a part of the stock solution was transferred in equal parts into other (identically dimensioned) vessels (of glass, polystyrene or polyethylene). As can be seen from FIG. 8b, a fresh severe decrease in the signal activity then occurs which in turn depends strongly on the material of the vessel used. The time information on the abscissa relates to the preparation of the stock solution.

What is claimed is:

1. A hapten tracer complex comprising a hapten linked directly or via a spacer group to an indicator component and an antibody which is bound specifically to said indicator component.

2. A hapten tracer complex as claimed in claim 1, wherein said indicator component is a chemiluminescent group.

3. A hapten tracer complex as claimed in claim 2, wherein said indicator component is acridinium acylsulfonamide, acridinium ester, luminol, isoluminol, dioxetane, oxalic acid ester, oxalamide, or a derivative of one of these compounds wherein said derivative compound contains a reactive group capable of linking said derivative compound to a hapten directly or via a spacer group.

4. A hapten tracer complex as claimed in claim 1, wherein said indicator component is a fluorescent group.

5. A hapten tracer complex as claimed in claim 1, wherein said indicator component is a biolumunescent group.

6. A hapten tracer complex as claimed in claim 1, wherein said indicator component is an electroluminescent group.

7. A hapten tracer complex as claimed in claim 1, wherein said indicator component is a phosphorescent group.

8. A hapten tracer complex as claimed in claim 1, wherein said antibody directed against said indicator component is a monoclonal antibody, a polyclonal antibody, or an antibody fragment.

9. A process for the preparation of a hapten tracer complex as claimed in claim 1, wherein said antibody directed against said indicator component is brought together in an aqueous solution with said hapten which is linked to said indicator component.

10. A test kit for carrying out an immunoassay for the detection of an antigen and/or hapten, comprising a hapten tracer complex as claimed in claim 1.

11. A test kit as claimed in claim 10, wherein said indicator complex of said hapten tracer complex is a luminescent indicator.

12. A test kit as claimed in claim 10, further comprising at least one antibody directed against said hapten, wherein said immunoassay is a competitive immunoassay.

13. A test kit as claimed in claim 10, further comprising magnetizable particles to which said antibodies directed against said hapten are bound.

14. A competitive immunoassay method for detection of an antigen or hapten in a sample, comprising the steps of:
   a) contacting the sample with an antibody directed against said antigen or hapten in the presence of a hapten tracer complex as claimed in claim 1;
   b) detecting the amount of said indicator component bound to said antibody directed against said antigen or hapten; and
   c) determining the amount of said antigen or hapten in the sample by means of appropriate calibration curves.

15. The process as claimed in claim 9, wherein said aqueous solution further comprises organic solvents for improving the solubility of said hapten linked to said indicator component, wherein said organic solvents are acetonitrile, dimethylformamide, dimethyl sulfoxide, or mixtures thereof.

16. A process for increasing the hydrophilicity of haptens linked directly or via a spacer group to an indicator component comprising the step of complexing said haptens with an antibody which binds specifically to the indicator component.

* * * * *